United States Patent [19]

Normann

[11] 3,957,036

[45] May 18, 1976

[54] METHOD AND APPARATUS FOR RECORDING ACTIVITY IN INTACT NERVES

[75] Inventor: Nils A. Normann, Houston, Tex.

[73] Assignee: Baylor College of Medicine, Houston, Tex.

[22] Filed: Feb. 3, 1975

[21] Appl. No.: 546,228

[52] U.S. Cl. .......................... 128/2.1 R; 128/2.1 E; 128/DIG. 4
[51] Int. Cl.$^2$............................................ A61B 5/04
[58] Field of Search ....... 128/2.1 E, 2.06 E, DIG. 4, 128/418, 419 C, 419 E, 419 P, 2.1 R, 404, 405, 407–411, 416, 417

[56] References Cited
UNITED STATES PATENTS

| | | | |
|---|---|---|---|
| 2,924,213 | 2/1960 | Fleck | 128/2.1 E |
| 3,157,181 | 11/1964 | McCarty | 128/2.1 E |
| 3,294,988 | 12/1966 | Packard | 128/2.1 R |
| 3,313,293 | 4/1967 | Cheesebrough | 128/2.1 E |
| 3,628,527 | 12/1971 | West | 128/2.1 E |
| 3,664,347 | 5/1972 | Harmjanz | 128/419 P |
| 3,749,100 | 7/1973 | Mosel | 128/407 |

OTHER PUBLICATIONS
Pollak, "Wave Shape of . . . Needles" Med. & Biol. Eng., Vol. 9, No. 6, Nov. 71, pp. 657–664.
Schaudinischky et al., "The Shape Conforming Electrode," Med. & Biol. Eng., Vol. 7, 1969, pp. 341–343.
Sonn et al., "A Prototype Flexible . . . Applications", Med. & Biol. Eng., Nov. 1974, pp. 778–790.

*Primary Examiner*—Robert W. Michell
*Assistant Examiner*—Lee S. Cohen
*Attorney, Agent, or Firm*—Fulbright & Jaworski

[57] ABSTRACT

A method and apparatus is provided which will attenuate bioelectric interference when measuring the activity in an intact nerve. An electrode probe is provided having first and second electrodes positioned on opposite sides of a thin, flexible, insulating carrier. The probe is inserted between the nerve to be measured and the underlying body tissue with one electrode contacting only the nerve and the second electrode contacting only the tissue. The nerve and the tissue thereby form in effect a Wheatstone bridge about the carrier and the symmetrical electrodes which thus provides a nulling effect on extraneous electrical potentials, while a measurement of nerve potentials appearing as a voltage difference between the electrodes provides a measurement of activity in the nerve. Additional, symmetrical pairs of electrodes may be positioned on the same carrier, and their outputs may electronically be combined for increasing the signal-to-noise ratio in the measurement. The apparatus may also be implanted in a body by covering the first electrode and the portion of the nerve in contact with the electrode with a second insulator which is preferably bonded to the first insulator, the electrode carrier, for electrically isolating both the first electrode and the segment of nerve from surrounding tissues.

7 Claims, 10 Drawing Figures

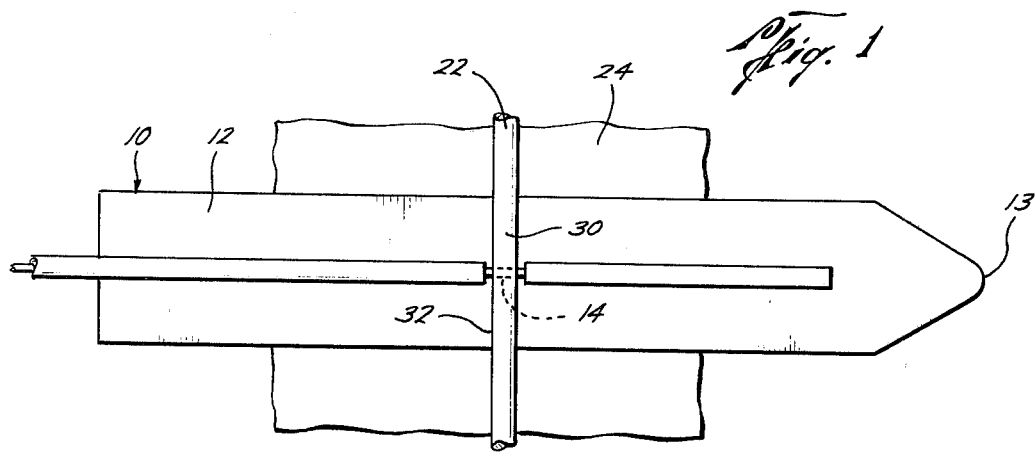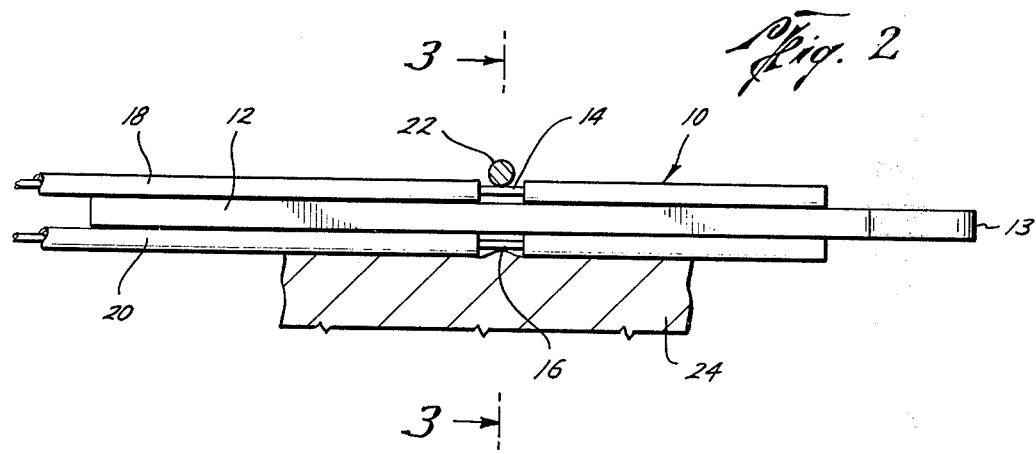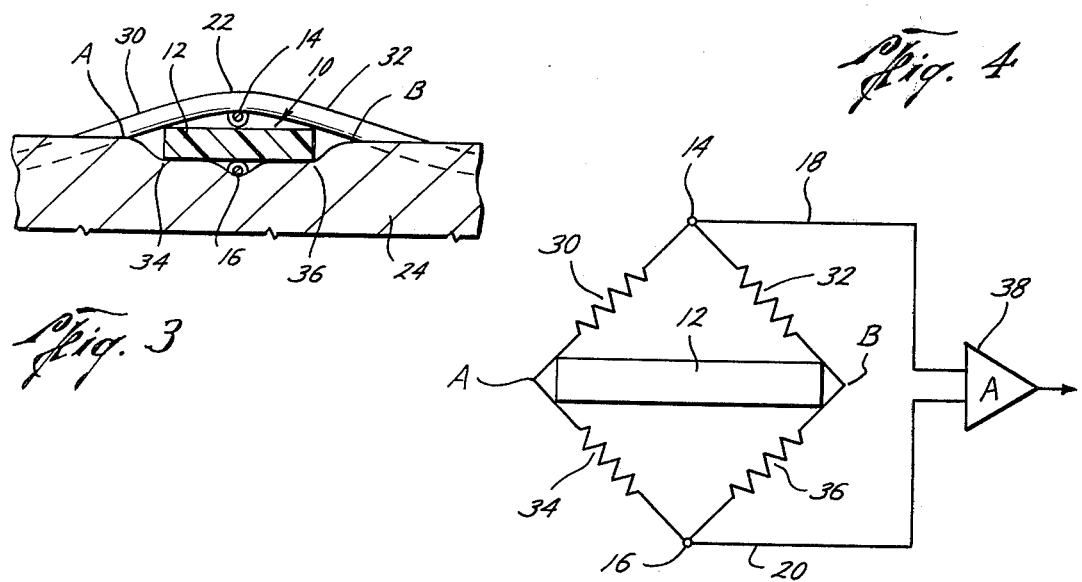

METHOD AND APPARATUS FOR RECORDING ACTIVITY IN INTACT NERVES

BACKGROUND OF THE INVENTION

This invention was conceived in the course of a grant from the National Heart and Lung Institute.

Peripheral nerves constitute communication lines in the body of humans and animals. As such, they serve both effector and reporting functions in a multitude of biologic control systems, voluntary as well as involuntary. It is therefore highly desirable to measure the activities in nerves, particularly in intact nerves, both for diagnostic purposes and as a research tool. However, in the past, bioelectric interferences, for example such as cardio-electric interference, present a problem when recording the activity in intact nerves. That is, an intact nerve has both ends of the isolated nerve segment to be measured attached to the body, and any extraneous potentials between the two points of attachment will be seen by a conventional electrode probe of the standard bipolar configuration. Typically, the potentials recorded from the surface of a multifiber, postganglionic, cardiac sympathetic nerve are in the range of one to ten microvolts in amplitude, peak to peak. If the nerve is left intact, and a conventional pair of electrode wires, for example four mm. or more apart, is placed under the isolated nerve segment, the many times larger electric fields of cardiac origin (ECG), will swamp the measurement.

Experimentally, in order to avoid bioelectric interference, the usual procedure is to create a one point attachment by severing the nerve, thus eliminating the extraneous field gradient along the nerve. However, in certain situations, it is mandatory or highly desirable that the nerve in question not be severed, but left intact such as:

1. Long-term nerve monitoring by means of implanted electrodes necessitates an intact nerve if impulse conduction is to be maintained;

2. Diagnostic nerve monitoring in humans, for example during surgery, should be atraumatic;

3. Experimentally, it is undesirable to sever the nerve as (a) this may alter the system under study, for example the measured target organ function, and (b) it may be desirable to record simultaneously both efferent and afferent traffic signals within the same nerve, particularly when these nerve activities are interdependent.

The present method and apparatus is directed to improvements in measuring and recording activities in intact nerves by achieving a nulling of extraneous bioelectric fields.

SUMMARY

The present invention is directed to a method of and an apparatus for measuring activities in intact nerves by achieving a nulling of extraneous bioelectric fields whereby the activities in the nerves may be measured without interference by extraneous potential fields.

The present invention is directed to providing an electrically insulated or non-conductive support carrier in which a first electrode is positioned on one side of the carrier, and a second electrode is positioned on the second side of the carrier diametrically opposed to the first electrode, the electrodes having identical and symmetrical contact areas. Hereby, when the probe is inserted between a segment of an intact nerve and body tissue, the nerve and the tissue form with a probe a Wheatstone bridge which achieves a nulling effect with respect to extraneous potentials, but allows measurement of the nerve activity by measuring the voltage between the electrodes.

A still further object of the present invention is the provision of a probe support carrier which is relatively thin, preferably flexible, and has a length greater than the width thus providing a Wheatstone bridge measurement configuration.

Still a further object of the present invention is the provision of a method and apparatus for measuring activity in an intact nerve attached to adjacent body tissue by placing first and second electrodes, having an insulating carrier positioned therebetween, in such a position that the first electrode is in contact with the nerve but out of contact with the tissue, and the second electrode is in contact with the tissue but out of contact with the nerve, and by measuring the voltage between the electrodes thus positioned.

Yet a still further object of the present invention is the provision of a plurality of symmetrical pairs of electrodes in which the output of each pair is connected to an amplifier and the outputs of the amplifiers are electronically combined for increasing the signal-to-noise ratio in the measurement.

Still a further object of the present invention is the method of implanting a probe within the body and measuring the activity in an intact nerve attached to adjacent body tissue, by placing first and second electrodes, having an insulating carrier positioned therebetween, in such a position that the first electrode is in contact with the nerve, and by covering the portion of the nerve resting on the carrier, in contact with the first electrode, with a second insulator for preventing contact of the first electrode and of the nerve segment with tissues surrounding the implanted electrode. The second electrode is positioned in contact with the underlying tissue but out of contact with the nerve. Voltages between electrodes are measured via leads attached to the electrodes extending out of the body. Alternatively, the electrodes may be directly connected to implantable microelectronics and the signals transmitted via telemetry. Preferably, the second insulator is bonded to the first insulator for isolating the segment of nerve and the first electrode from tissue.

Other and further objects, features and advantages will be apparent from the following description of presently preferred embodiments of the invention, given for the purpose of disclosure and taken in conjunction with the accompanying drawings.

BRIEF DESCRIPTION OF THE DRAWINGS

FIG. 1 is a top elevational view of the preferred embodiment of the present invention in use measuring activity in a nerve, FIG. 2 is a side elevational view of the apparatus of FIG. 1, FIG. 3 is a cross-sectional view taken along the line 3—3 of FIG. 2, FIG. 4 is an electrical schematic of the electrical analog of the device of the present invention in use measuring activity of a nerve as illustrated in FIGS. 1–3.

DESCRIPTION OF THE PREFERRED EMBODIMENT

Figure 5:
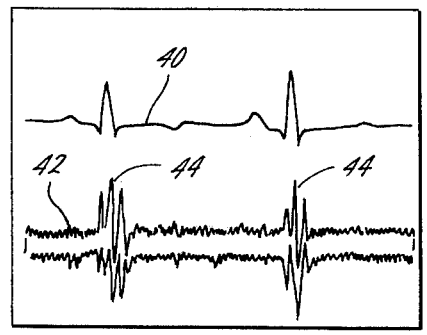
FIG. 5 is a graph illustrating an ECG signal along with a graph of raw data activity in a nerve as measured by a prior art electrode probe, FIG. 6 are graphs of the data shown in FIG. 5 after processing of the nerve signals.

Referring now to the drawings, and particularly to FIGS. 1-3, the electrode probe of the present invention is generally indicated by the reference numeral 10 which generally includes a support carrier 12, a first electrode 14 and a second electrode 16. The carrier is made of any suitable insulating or electrically non-conductive, preferably flexible material such as a plastic sold under the name Mylar by DuPont. The first electrode 14 is mounted on one side of the carrier 12 and the electrode 16 is mounted on the opposite side of the carrier 12 in precise opposition to the electrode 14 so as to be diametrically or directly opposed thereto as will be more fully discussed hereinafter.

Preferably, the electrodes 14 and 16 may be formed from insulated electrode wires 18 and 20, respectively, which may be any suitable material such as silver, steel or platinum in which the insulation from the wires 18 and 20 are removed for a short and identical segments forming the electrodes 14 and 16. Therefore, the electrodes 14 and 16 provide symmetrical areas of electrical contact for measuring purposes. In addition, the wires 18 and 20 form leads extending from the electrodes 14 and 16 to suitable measuring instruments for measuring the voltage between the electrodes 14 and 16.

While the carrier 12 may be of various configurations, shapes and sizes, one satisfactory shape is as shown in FIGS. 1-3 in which the carrier 12 is generally rectangular in cross section, but has a generally rounded end 13 for ease of inserting the probe 10 between the nerve 22 and tissue 24 and in which the carrier was approximately 5 mm. wide, 0.025 mm. thick, and approximately 2 cm. in length.

The purpose of the electrode probe 10 is to measure the activity in an intact nerve such as nerve 22 which is normally adjacent tissue 24 in the body of a human or an animal. As shown in FIGS. 1-3, a segment of the nerve 22 is separated from the tissue 24 and the probe 10 is inserted between the nerve 22 and the tissue 24 and positioned so that one of the electrodes, such as 14, is placed in contact with the nerve 22, but out of contact with the tissue 24, and the second electrode, such as 16, is placed in contact with the tissue 24, and out of contact with the nerve 14.

When the electrode probe 10 is inserted as shown in FIGS. 1-3, the electrodes 14 and 16, in combination with portions of the nerve 22 and the tissue 24, form in effect a Wheatstone bridge which, while measuring the activity in the intact nerve, will attenuate or null extraneous electrical fields such as might be caused by bioelectric interference.

Referring to the electrical analog schematic of FIG. 4, portions of the nerve 22 and tissue 24 form the resistances 30, 32, 34, and 36 of the bridge circuit. Thus, resistances 30 and 32 correspond to nerve portions 30 and 32 leading in opposite directions from the electrode 14 to contact points A and B with the tissue 14. Similarly, resistances 34 and 36 correspond to the tissue 24 leading in opposite directions from the electrode 16 to the points A and B where the tissue 24 joins the nerve 22. Of course, the nerve signals will propagate from point A to B of the Wheatstone bridge only through the nerve 22 and thus pass only through the resistances 30 and 32 and not through resistances 34 and 36. However, any electrical potential difference between the points A and B caused by extraneous potentials, such as cardio-electric (ECG) interference, will flow through both the nerve 22 and the tissue 24 and thus will go through all of the resistances 30, 32, 34 and 36. Therefore, from the general Wheatstone bridge principle, it is noted that if the ratio between resistances 30 and 32 matches the ratio between resistances 34 and 36, then any electrical potential difference between points A and B, as induced by a bioelectrical interference, will be nulled as measured at the electrodes 14 and 16.

A nerve action potential, however, will be measured and recorded as it propagates from point A to electrode 14 to point B, or, in the reverse direction. Therefore, using the basic principles of the Wheatstone bridge, the current flowing through the bridge does not give rise to any potential difference between the opposing branch electrodes 14 and 16 as long as the bridge is balanced. If, however, a source of current is introduced in one arm of the bridge, thus through resistances 30 and 32, then a potential difference would exist between the electrodes 14 and 16 which, through the leads 18 and 20, can be measured by a differential amplifier 38. With respect to the input to the differential amplifier 38, the result is that electrical fields, such as those of cardiac origin (ECG), will appear as common mode signals, while nerve potentials will appear as difference signals. Therefore, it is important that the configuration of the electrodes 14 and 16 and their directly opposing position relative to each other and the carrier 12 be such that the ratios between the resistances of the Wheatstone bridge formed by the probe 10 with the nerve and the tissue be such as to attenuate or null the extraneous fields which may be encountered and which can interfere with the signals being measured in the nerve.

While the invention is applicable to measuring any peripheral nerve, in utilizing the electrode probe 10 of the present invention, the activities in cardiac autonomic nerves within the chest have been measured and recorded without significant cardio-electric interference. For illustrative purposes, a comparison has been made between recordings obtained with the probe 10 of the present invention as compared with recordings obtained with an electrode of standard configuration. As previously indicated, standard side-by-side electrode wires, placed under an intact nerve segment within the chest, are likely to pick up ECG potentials which will saturate an amplifier designed for amplification of nerve potential. Therefore, a conventional electrode probe was constructed having two electrode wires mounted only 2 mm. apart and on the same side of a carrier. The closeness of the two side-by-side conventional electrodes drastically attenuates the amplitude both of the nerve action potentials and of the ECG field and while such a conventional electrode performs poorly for recording potentials from a multifiber nerve, it does keep the ECG interference potentials within the limit of the amplifier.

Figure 6:
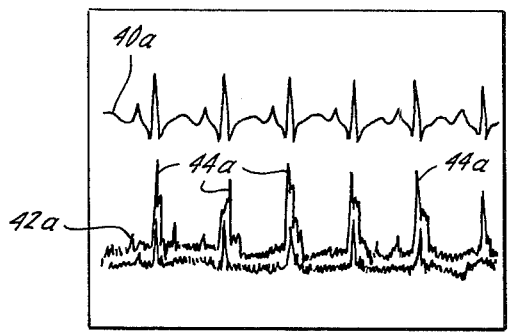
Figure 7:
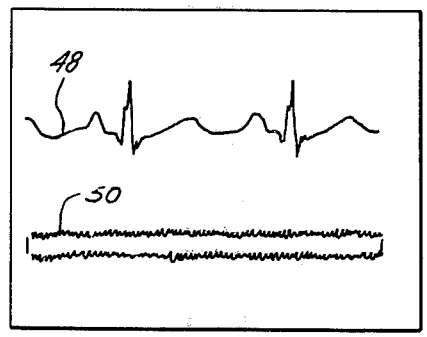
FIG. 7 is a graph of an ECG along with a graph of raw data nerve activity obtained by the probe of the present invention.

The graphs in FIG. 5–8 are recordings made (1) with a conventional electrode probe (FIGS. 5 and 6) and (2) made with the electrode probe 10 of the present invention (FIGS. 7 and 8), in which the electrodes were placed under the intact left phrenic nerve of a dog, 2 cm. cranially to the aortic arch. The nerve tracings in FIGS. 5 and 7 are "raw" data obtained during the period of little neural activity. The nerve tracings in FIGS. 6 and 8 have been processed by means of rectification and integration.

Therefore, graph 5 indicates an ECG signal 40 and the raw data 42 obtained from the nerve tracings. It is apparent that the ECG signals are affecting the nerve signals 42 at points 44 on the nerve tracings 42. However, in FIG. 7, using the electrode probe 10 of the present invention, the ECG signal 48 and the raw data tracings 50 obtained from the nerve demonstrate the nulling effect by the probe 10 on the ECG signal.

Figure 8:
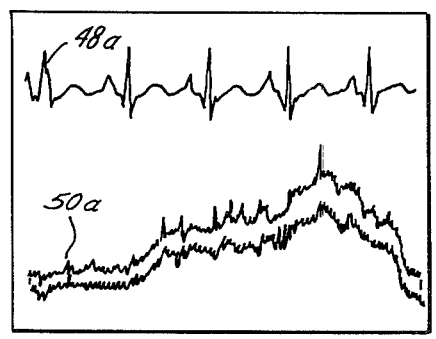
FIG. 8 is a graph of the data shown in FIG. 7 after the nerve signal data have been processed.

As mentioned, the graphs in FIGS. 6 and 8 correspond to the graphs of FIGS. 5 and 7, respectively, in which the nerve tracings have been processed by means of rectification and integration. Thus, FIG. 6 shows the ECG signal 40a and the processed nerve tracing 42a which still include the ECG signals 44a. However, FIG. 8, using the present invention shows an ECG signal 48a, and a processed nerve activity signal 50a in which the ECG signals have been nulled. The increase in nerve activity seen in nerve recording 50a in FIG. 8 represents phrenic nerve outflow during an inspiratory effort. Therefore, the nulling effect of the ECG signals by the present invention is illustrated from a comparison of the output from a conventional probe in FIGS. 5 and 6 with the output from the improved probe of the present invention as shown in FIGS. 7 and 8.

Figure 9:
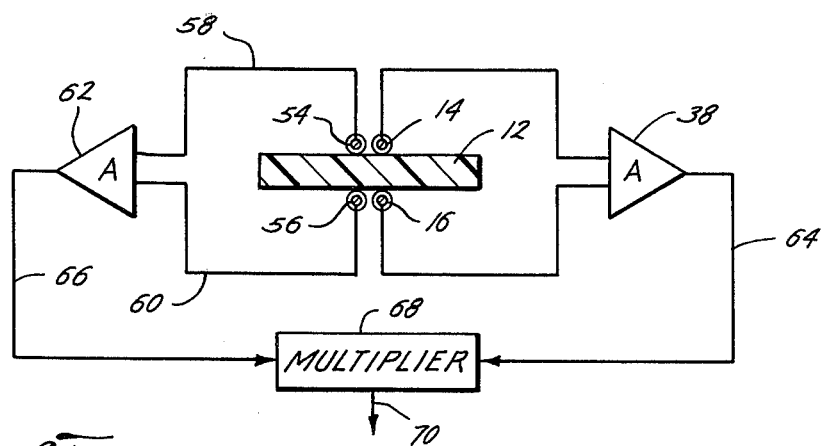
FIG. 9 is a cross-sectional view of the probe of the present invention utilizing a plurality of pairs of electrodes.

It is desirable to increase the signal-to-noise ratio in measuring the acitivity in a nerve. This may be accomplished in the present invention, as best seen in FIG. 9, by adding additional pairs of electrodes on the carrier 12 and then electronically combining the signals obtained with the pairs of electrodes. Therefore, additional electrodes such as the electrodes 54 and 56, which are similar to electrodes 14 and 16, may be placed on opposite sides of the carrier 12 in opposition to each other. Leads 58 and 60 connected to the additional pair of electrodes 54 and 56, respectively, are fed to a second amplifier 62. The outputs 64 and 66 from the amplifiers 38 and 62, respectively, may be suitably combined, such as by multiplier 68 to provide an output 70. Since noise is generally random, the combining of the signals from the amplifier 38 and 62 will tend to reduce the noise while increasing the nerve activity signals common to the two channels, thereby providing a higher signal-to-noise ratio.

Figure 10:
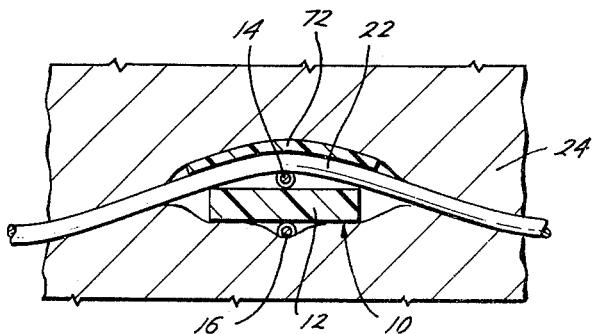
FIG. 10 is a cross-sectional view of the apparatus of FIGS. 1-3 shown implanted in a body.

As indicated, it may be desirable to implant the electrode probe 10 in the body for long-term nerve monitoring. In such a case, it is desired that the carrier 10 be of a material that is well tolerated by the tissue 24 and any suitable material may be used such as the plastic sold under the trademark "Silastic" sold by Dow Corning. Referring now to FIG. 10, the electrode probe 10 is shown in cross section implanted in a body in which the electrode 14 is in contact with the nerve 22 and the electrode 16 is in contact with the tissue 24. However, when the probe 10 is implanted, the tissue 24 should not be allowed to contact the electrode 14 nor the isolated segment of nerve 22 as this would short out the signals to be measured. Therefore, a second insulator 72, usually in semifluid form such as an RTV, is applied over the nerve 22 and the electrode 14 to isolate them from surrounding tissues 24. The second insulator 72 may be of any suitable material such as RTV silicone rubber which will bond itself to the carrier 12 and thus isolate the electrode 14 and the segment of nerve 22 from other undesired electrically conducting elements.

The method of the present invention is apparent from the foregoing description of a preferred embodiment of the apparatus. The method comprehends a method of measuring activity in an intact nerve attached to adjacent body tissue by placing first and second electrodes having an insulator positioned therebetween in such a position that the first electrode is in contact with the nerve, but out of contact with the tissue, and the second electrode is in contact with the tissue but out of contact with the nerve, and by measuring the voltage between the electrodes thus positioned. The method further comprehends implanting the probe in a body and covering the first electrode and the portion of the nerve in contact with the first electrode with a second insulator for preventing contact with surrounding tissues. The method further comprehends attachment between the second insulator to the first insulator.

The present invention, therefore, is well adapted to carry out the objects and attain the ends and advantages mentioned as well as others inherent therein. While a presently preferred embodiment of the invention has been given for the purpose of disclosure, numerous changes may be made without departing from the spirit and scope of the invention.

What is claimed is:

1. An electrode probe for measuring activity in intact nerves comprising,
    an electrically non-conductive thin and substantially flat carrier having first and second sides opposite to each other,
    a first electrode positioned and attached on the first side of the carrier,
    a second electrode positioned and attached on the second side of the carrier and positioned diametrically opposed to the first electrode,
    electrically conductive contact areas of the two electrodes being of the same size and located symmetrically in precise opposition to each other,
    an insulated wire connected to each of the electrodes, and
    differential amplifier means connected to said insulated wires measuring the voltage difference between said electrodes.

2. The apparatus of claim 1 wherein the carrier is a flexible material, and has a length greater than its thickness.

3. The apparatus of claim 1 wherein the size of the contact areas on the two electrodes is substantially equal to the diameter of the nerve to be measured.

4. An electrode probe for measuring activity in intact nerves comprising,
    an electrically non-conductive thin and substantially flat carrier having first and second sides opposite to each other,
    a first electrode positioned and attached on the first side of the carrier,
    a second electrode positioned and attached on the second side of the carrier and positioned diametrically opposed to the first electrode,
    electrically conductive contact areas of the first and second electrodes being of the same size and located symmetrically in precise opposition to each other, an insulated wire connected to each of the first and second electrodes, a third electrode positioned on the first side of the carrier, a fourth electrode positioned on the second side of the carrier and positioned diametrically opposed to the third electrode, electrically conductive contact areas of the third and fourth electrodes being of the same size and located symmetrically in opposition to each other, an insulated wire connected to each of the third and fourth electrodes, a first amplifier connected to the insulated wires of the first and second electrodes, a second amplifier connected to the insulated wires of the third and fourth electrodes, combining means connected to the outputs of the first and second amplifiers for increasing the signal-to-noise ratio of the output nerve signals.

5. A method of measuring activity in an intact nerve attached to adjacent body tissue while nulling extraneous electrical potentials in the body comprising, placing an insulating carrier having first and second identical electrodes positioned diametrically on opposite sides of the carrier in the body, positioning the carrier with the first electrode in contact with the nerve but out of contact with the tissue and the second electrode in contact with the tissue but out of contact with the nerve, and measuring the voltage between the electrodes whereby activity in the intact nerve is measured but extraneous electrical potentials in the body are nulled.

6. A method of implanting a probe and measuring the activity of an intact nerve attached to adjacent body tissue while nulling extraneous electrical potentials in the body comprising, placing an insulating carrier having first and second identical electrodes positioned diametrically on opposite sides of the carrier in the body, positioning the carrier with the first electrode in contact with the nerve but out of contact with the tissue and the second electrode in contact with the tissue but out of contact with the nerve, covering the first electrode and the portion of the nerve in contact with the first electrode with an insulator for preventing contact with surrounding tissues, and measuring the voltage between the electrodes.

7. The method of claim 5 including, attaching the insulator to the insulating carrier.

* * * * *